United States Patent
Vogl et al.

(10) Patent No.: US 9,314,200 B2
(45) Date of Patent: Apr. 19, 2016

(54) LANCING DEVICE FOR COLLECTING BODY FLUID SAMPLES

(71) Applicant: Gerresheimer Regensburg GmbH, Regensburg (DE)

(72) Inventors: Maximilian Vogl, Mantel (DE); Andreas Fraas, Amberg (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 33 days.

(21) Appl. No.: 14/137,327

(22) Filed: Dec. 20, 2013

(65) Prior Publication Data
US 2014/0180322 A1 Jun. 26, 2014

(30) Foreign Application Priority Data

Dec. 21, 2012 (DE) .................. 10 2012 112 882

(51) Int. Cl.
*A61B 5/151* (2006.01)
*A61B 5/15* (2006.01)

(52) U.S. Cl.
CPC .............. *A61B 5/1519* (2013.01); *A61B 5/1411* (2013.01); *A61B 5/150022* (2013.01); *A61B 5/15101* (2013.01); *A61B 5/15113* (2013.01); *A61B 5/15194* (2013.01); *A61B 5/150412* (2013.01); *A61B 5/150687* (2013.01); *A61B 5/150183* (2013.01)

(58) Field of Classification Search
CPC ............... A61B 5/150183; A61B 5/15113; A61B 5/1411; A61B 5/151; A61B 5/150549; A61B 5/15142; A61B 5/15186; A61B 5/15188; A61B 5/150015; A61B 5/150687; A61B 5/150534; A61B 5/15058; A61B 5/150633; A61B 5/150664; A61B 5/150694; A61B 5/150541; A61B 5/150557; A61B 5/150564; A61B 5/150587; A61B 5/150595; A61B 5/150603; A61B 5/15061; A61B 5/150618; A61B 5/150625; A61B 5/15064; A61B 5/150648; A61B 5/150656; A61B 5/150671; A61B 5/150679; A61B 5/150702; A61B 5/150709; A61B 1/00137; A61B 5/150351
USPC .......................... 606/181–183; 600/585, 583; 604/164.08

See application file for complete search history.

(56) References Cited

U.S. PATENT DOCUMENTS

| 4,887,998 A * | 12/1989 | Martin et al. ................. 604/110 |
| 2006/0247670 A1 | 11/2006 | LeVaughn et al. |
| 2010/0324582 A1 | 12/2010 | Nicholls et al. |

OTHER PUBLICATIONS

Examination Report issued on Jul. 24, 2013, from the German Patent Office for German Patent Application No. 10 2012 112 882.0.

* cited by examiner

*Primary Examiner* — Sarah W Aleman
*Assistant Examiner* — Socrates L Boutsikaris
(74) *Attorney, Agent, or Firm* — Lathrop & Gage LLP

(57) ABSTRACT

A lancing device for collecting body fluid samples with a body at the end of which an endcap is arranged. The endcap has a positioning surface with an outlet opening. The device further comprises a socket to receive at least one lancet, which is interchangeably clamped in the body, a clamping device, and a release mechanism, with which the lancet is clamped inside the body. The lancing procedure is initiated with the tip of the lancet emerging through the outlet opening. An ejection device is used to eject a used lancet. The endcap is functionally coupled with the ejection device in such a way that, when the ejection device is actuated, the endcap is held pivotably on the body so that it can swing out of the path of the lancet.

20 Claims, 9 Drawing Sheets

LANCING DEVICE FOR COLLECTING BODY FLUID SAMPLES

CROSS REFERENCE TO RELATED APPLICATIONS

Figure 1:
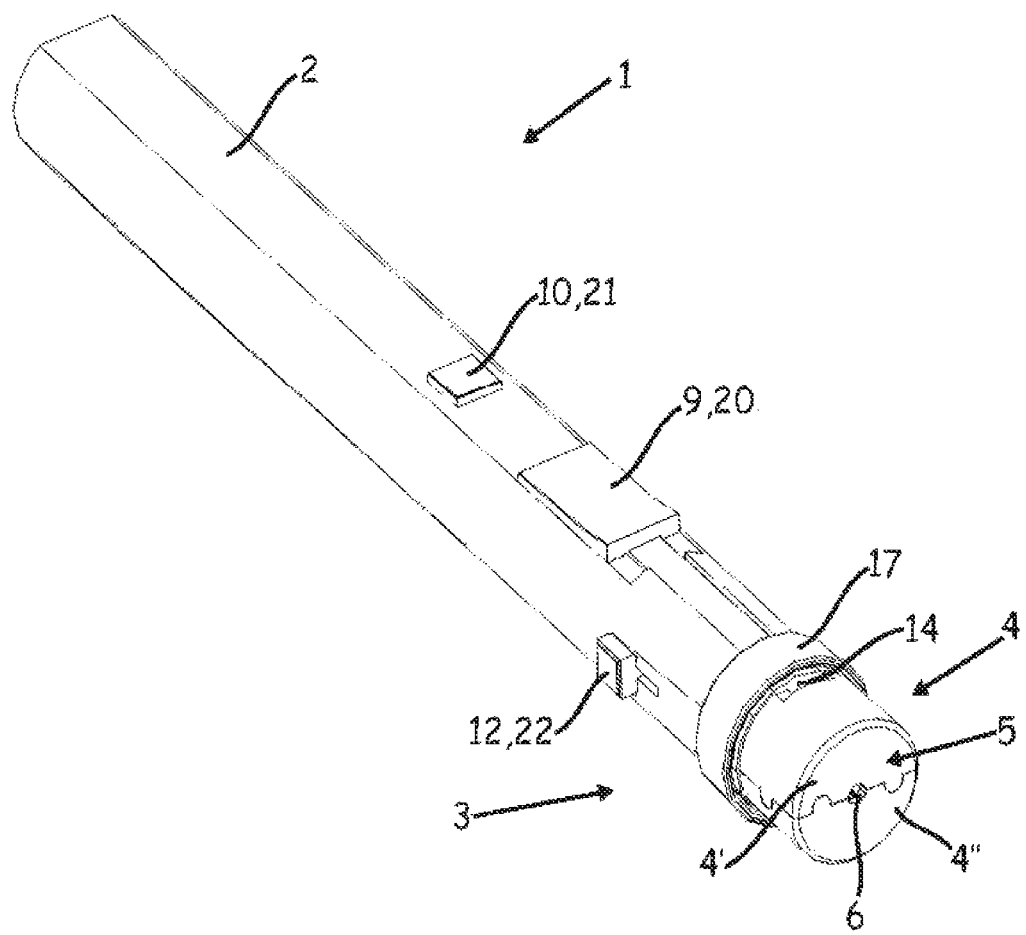

This application claims the benefit of and priority to German Application No. 10 2012 112 882.0, filed on Dec. 21, 2012, which is hereby incorporated by reference in its entirety.

DESCRIPTION

The invention relates to a lancing device for collecting body fluid samples according to the preamble of claim 1.

Using conventional lancing devices at home often involves many different steps and this makes them difficult for patients to use, particularly if these patients have motor disorders. In the known systems, changing the lancet is particularly awkward and involves a whole series of steps. This includes taking off the cap of the lancing device and putting it back on again. One of the problems observed for patients is that the cap is too firmly seated and they cannot remove it and also that they lose the cap, thus rendering the lancing device unusable. Also they put the cap on at the wrong angle so that the device does not operate correctly and consequently the lancing results obtained are not appropriate for the indication.

A lancing device known from WO 2006/083676 A2 has a large number of lancets. Here the lancets are arranged in series in the lancing device, one behind the other. However, to prevent the next lancet being exposed before use, it is provided with an endcap, which must be removed before the lancing device can be used which means that the above-mentioned problems can occur.

Some solutions to these problems are offered by lancing devices with endcaps that are attached to the housing by a hinge for example and can be folded out of the way of the movement path necessary for ejection before changing or ejecting a used lancet. This therefore gets round the problem of losing the cap but does nothing to resolve the problem of the additional steps required to change the lancet. Other solutions provide a connecting strap between the housing of the lancing device and the endcap. However, once again, this only solves the problem of losing the cap.

The object of the invention is therefore to develop a lancing device according to the preamble of claim 1 such that it allows easy and user-friendly replacement of used lancets.

The object is achieved by a lancing device with the characteristics of claim 1. Advantageous embodiments of the invention are to be found in the sub-claims.

The lancing device for collecting body fluid samples according to the invention substantially comprises the following:
a) a body, at the end of which an endcap is arranged, said endcap having a positioning surface with an outlet opening,
b) a socket to receive at least one lancet, which is interchangeably clamped in the body,
c) a clamping device and a release mechanism, with which the lancet is clamped inside the body and the lancing process of the lancet is initiated, the tip of said lancet emerging through the outlet opening during the lancing procedure,
d) an ejection device to eject a used lancet.

Provision is made for the endcap to be functionally coupled with the ejection device in such a way that, when the ejection device is actuated, said endcap is held on the body so that is can swing out of the path of the lancet, preferably automatically.

Because the endcap of the lancing device is functionally coupled with the ejection device, actuating the ejection device not only pushes the lancet arranged in the lancing device towards the endcap but, because of the functional coupling of the ejection device with the endcap, the endcap also swings out simultaneously so that the lancet can be ejected from the lancing device without its course being impeded by the endcap. The user does not need to move the endcap out of the way of the lancet in a separate step before actuating the ejection device. At the same time the endcap is held securely and captively on the body, even when it has adopted the open position, in which the lancet arranged in the lancing device can be ejected. The endcap is preferably pivotably mounted so that it can swivel perpendicularly to the direction of displacement of the lancet. However, according to the invention, it is also possible for the endcap to be pivotably mounted parallel to the direction of displacement of the lancet. The embodiment of the lancing device according to the invention provides the patient or user with a lancing device that is much simpler to use, especially if the patient or user has motor problems.

Moreover, the functional coupling of the endcap of the lancing device with its ejection device is preferably mechanical in nature so that no additional motor elements have to be incorporated within the lancing device to cause the endcap to swivel. This also has the advantage that the installation space of the lancing device can be kept relatively small and also minimises the amount of installation required. However, it is, of course, also possible to couple the ejection device and the endcap electronically/electrically and to initiate the pivoting of the endcap by motor actuation.

In a first advantageous embodiment of the invention the endcap is pivotably mounted on the body by means of a pivot joint, said pivot joint being spring loaded by a spring element. This embodiment provides simple automatic pivoting of the endcap from a closed position into the open position, if the spring element of the spring-loaded pivot joint is at least partially relaxed on actuation of the ejection device. Because of the spring loading of the pivot joint, it has proven expedient to lock the endcap of the lancing device against its body in the closed position so that the endcap cannot unintentionally swing open but rather is securely held in the closed position. This interlocking is automatically released when the ejection device is operated so that, due to the spring-loaded pivot joint, the endcap can be automatically moved from the closed position into the open position.

According to an additional advantageous idea, the endcap comprises multiple portions, most preferably two portions, each portion of the endcap being mounted on the body by means of a pivot joint spring loaded by a spring element. For example, this means that, after a lancet has been ejected from the lancing device, a new lancet can simply be inserted into the socket of the lancing device because the multiple portions of the endcap provide a good haptic signal as to where the lancet should be inserted into the lancing device. Particularly for diabetics, who often cannot see very well without vision aids, this type of haptic guide makes it much simpler to introduce a new lancet into the socket of the lancing device.

So that the separate portions of the endcap can be locked together relative to the body, it has proven useful to arrange interlocking, detachable locking elements, preferably snap-in hooks and corresponding snap-in elements, on the individual portions of the endcap. This does away with the need to arrange individual locking elements between the body and each individual portion of the endcap. Interlocking the individual portions of the endcap also means that the entire endcap is locked relative to the body of the lancing device, each individual pivot joint of the individual portions being spring-loaded in the locked position, which corresponds to the closed position of the endcap. These interlocks are automatically released when the ejection device is actuated, so that, due to the spring-loaded pivot joints of the individual portions, the endcap is automatically moved out of the closed position into the open position as one unit.

According to a stand-alone idea of the invention, the endcap is functionally coupled with the clamping device so that, when the lancet is clamped in the body, said endcap can automatically pivot from the open position into a closed position. This measure further simplifies handling of the lancing device according to the invention. It means that the user does not need to move the endcap from the open position into the closed position in a separate processing step before actuating the clamping device, since this happens automatically. Once again, the functional coupling of the endcap of the lancing device with the clamping device is preferably mechanical in nature so that no additional motor elements have to be incorporated within the lancing device to swivel or close the endcap. Again this has the advantage that the installation space of the lancing device can be kept relatively small and also minimises the amount of installation required. However, it is, of course, also possible to couple the clamping device and the endcap electronically/electrically and to initiate pivoting of the endcap by motor actuation.

Also the clamping device preferably comprises a slider element, which can be slid at least partially over the endcap while the lancet is clamped in the body, this causes the endcap to pivot from an open position into a closed position. This configuration of the clamping device provides a simple mechanical method for closing the endcap. Although in this configuration the endcap is closed by the clamping device, even if said clamping device is motor operated, and the slider element in a purely mechanical way, closure of the endcap by motor-actuation is also conceivable, however, even in this case, closure is initiated by actuating the clamping device.

Particularly if the body of the lancing device is substantially cylindrical, it has proven advantageous to design the slider element as a locking ring arranged around the circumference of the cylindrical body of the lancing device. Also with endcaps comprising more than one portion, this guarantees that all portions of the endcap move as a unit from the open position into the closed position for clamping of the lancet.

To ensure that the individual portions of the endcap are correctly positioned relative to each other after each closure, the individual portions of the endcap comprise interlocking latching means. This ensures that the positioning surface of the lancing device is even and regular every time the endcap closes so that the user can position it evenly on the application site to perform the lancing procedure. This prevents incorrect lancing procedures because, if the positioning surface of the lancing device is not even, the depth of penetration of the lancet may be incorrect.

To make the clamping device easy to operate, it has a clamping slider, which is preferably arranged on the surface of the body. The lancet can easily be clamped by sliding this clamping slider towards the end of the lancing device where the endcap is located, said clamping slider being simultaneously slid towards the endcap end of the lancing device, due to the preferably integral formation or direct coupling of this clamping slider and the slider element. This causes the slider element or the locking ring to slide over the portions of the endcap thereby closing it when the locking elements reach their locking position. As soon as the locking elements have reached their locking position, the lancet is also preclamped in the socket of the lancing device body. If the clamping slider is now released, it and the closing element return to their original position.

The release mechanism advantageously comprises a release element, preferably arranged on the surface of the body and most preferably designed as a release button. The lancing procedure is initiated by actuating the release element or the release button. The clamped lancet held in a lancet body is now pushed towards the endcap end of the lancing device by releasing the tension until the tip of the lancet protrudes through the opening in the positioning surface of the endcap to the desired depth, which can be adjusted on the lancing device. As the lancet is pushed out it is again clamped so that, once its tip has emerged from the opening in the positioning surface of the endcap to the desired penetration depth, it is retracted back inside the lancing device due to tension. The used lancet is now kept safely inside the lancing device and can be ejected from it into the provided disposal container by performing an ejection process and be duly disposed of.

The ejection device has an ejection slider, preferably also arranged on the surface of the body, to eject a lancet. When the ejection device is actuated or the ejection slider is pushed, a contact element disengages the locking elements, which preferably comprise snap-in hooks and corresponding snap-in elements, during ejection of a used lancet. This swivels the endcap or the portions thereof out of the closed position and into the open position, so that the used lancet can be ejected from the lancing device when the ejection slider has reached its extreme position at the endcap end of the lancing device. From this position the ejection slider automatically returns to its original position when it is released due to pre-tensioning.

Additional aims, advantages, characteristics and potential applications of the present invention are illustrated by the following description of practical examples with the aid of drawings. All characteristics that are described and/or diagrammatically represented constitute, per se or in any reasonable combination, the object of the present invention, regardless of whether they are summarised in the claims or referenced.

Figure 2:
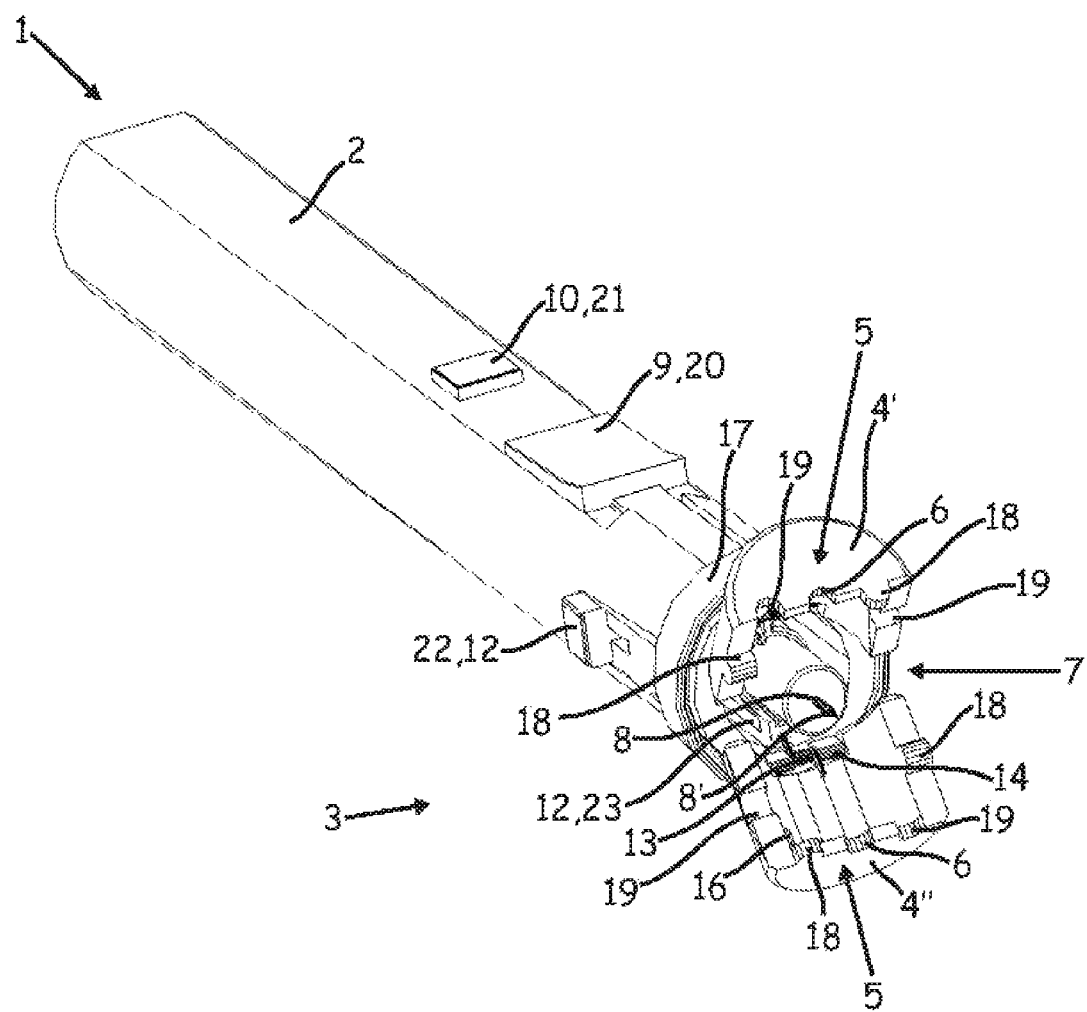
Figure 3:
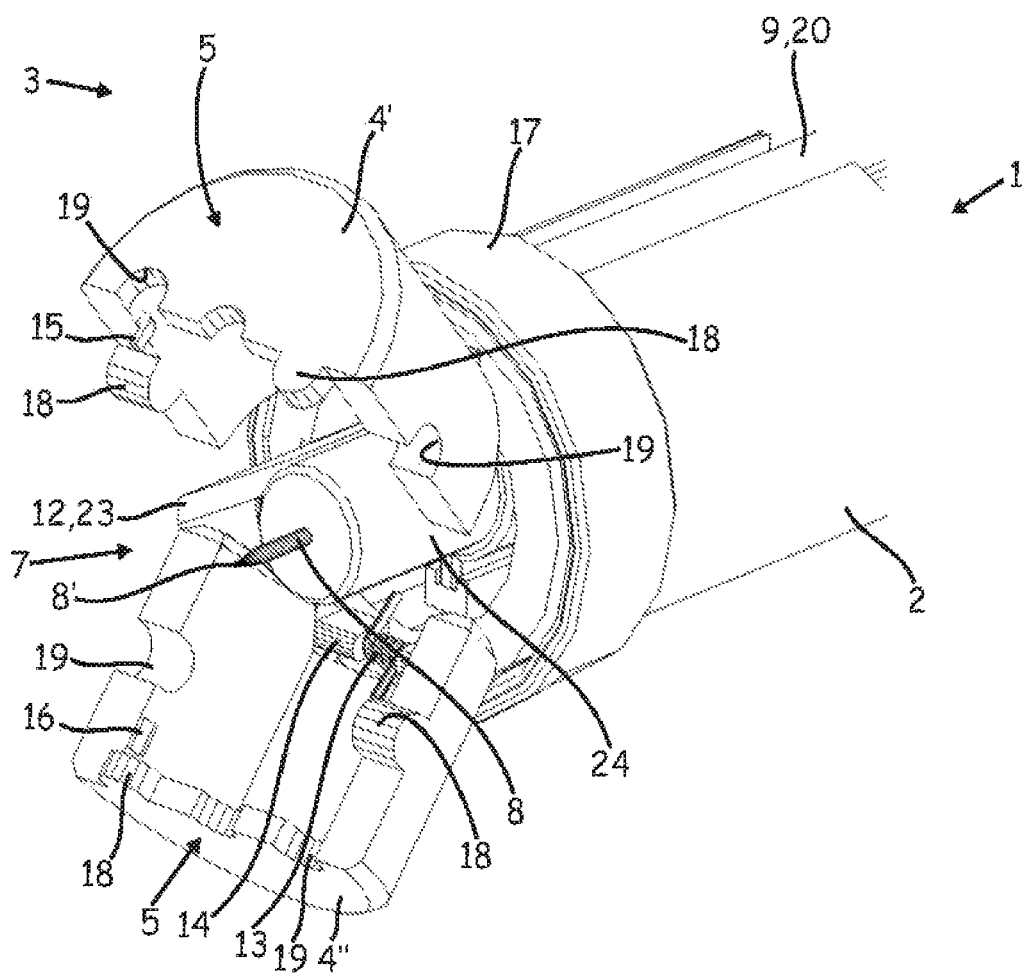
Figure 4:
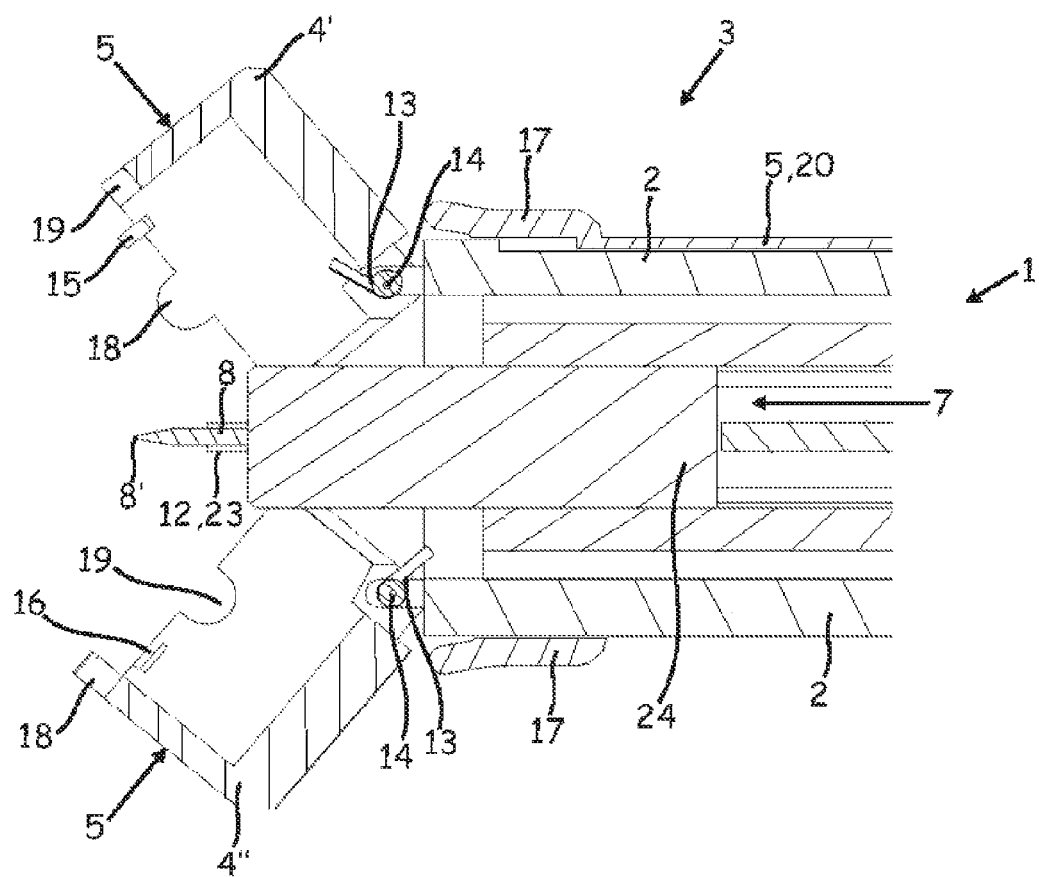
Figure 5:
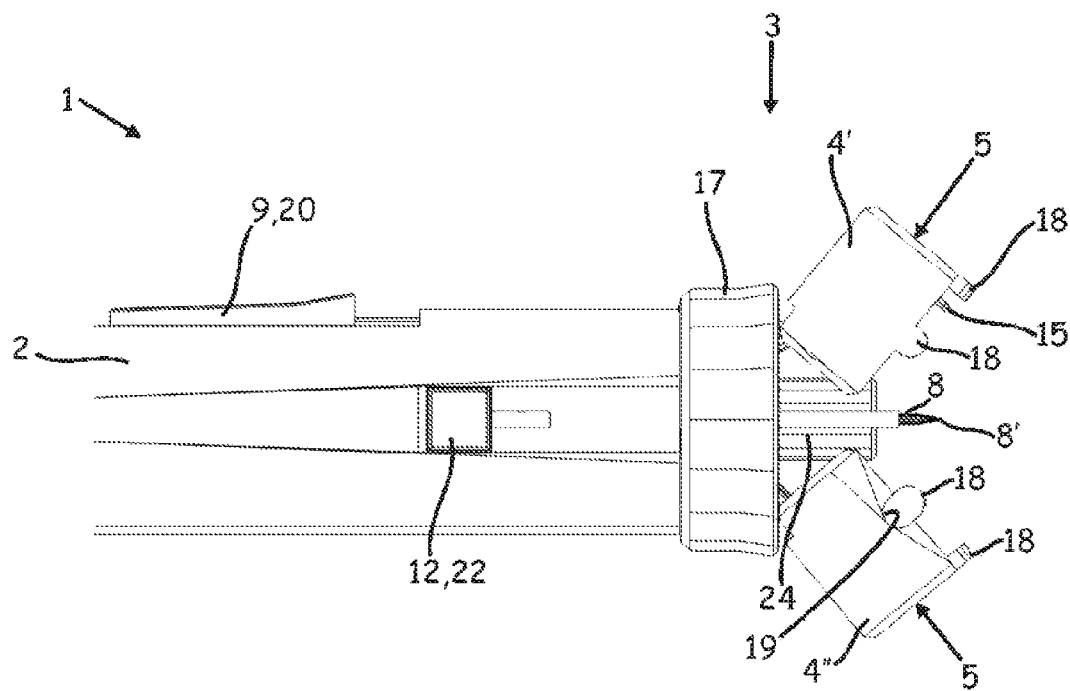
Figure 6:
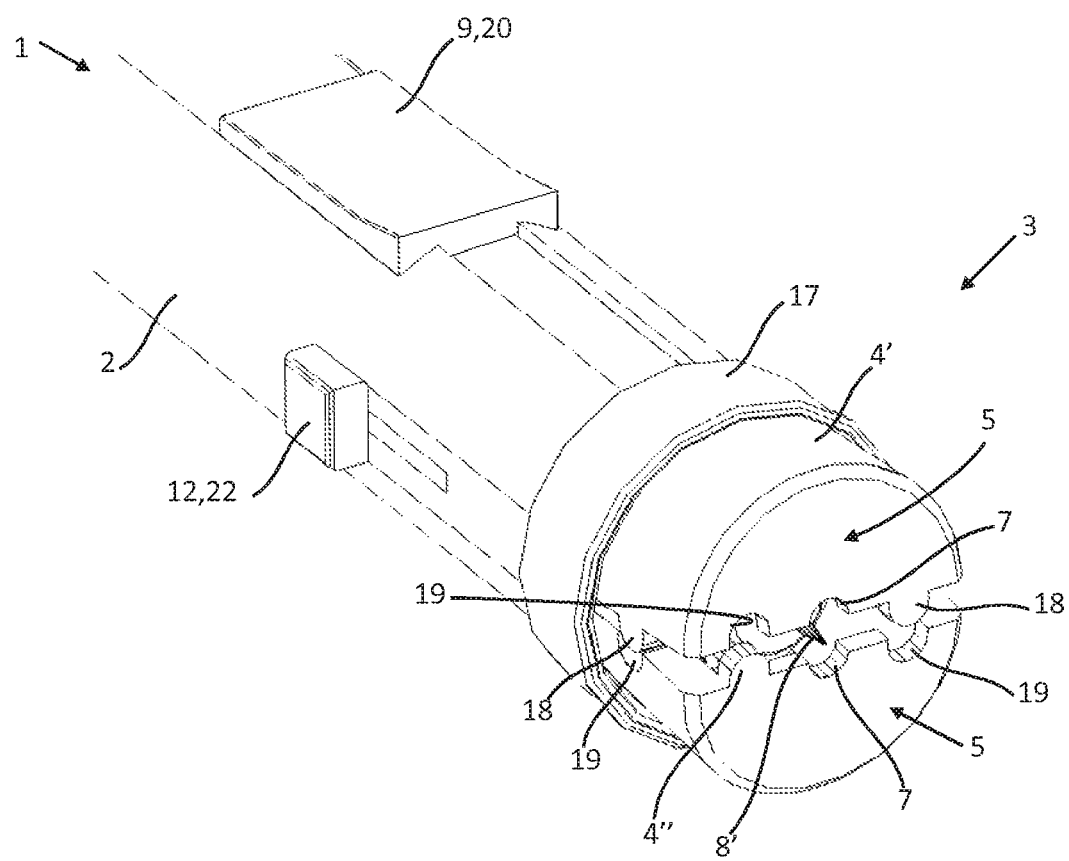
Figure 7:
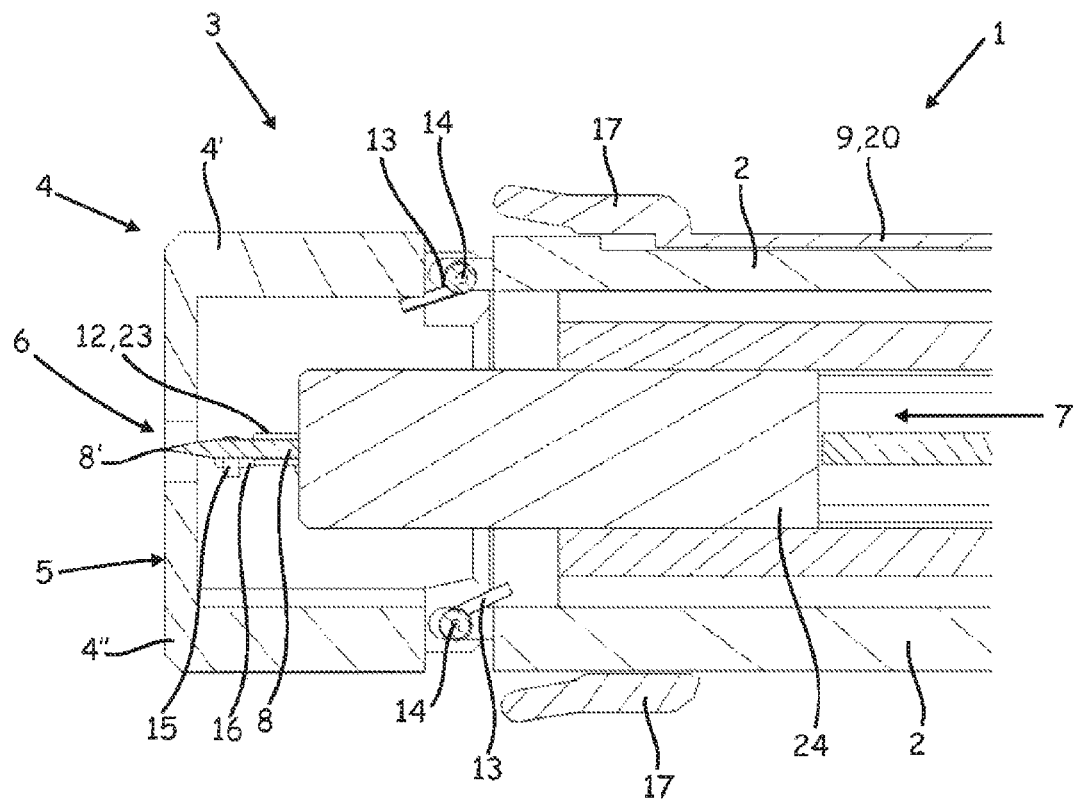
Figure 8:
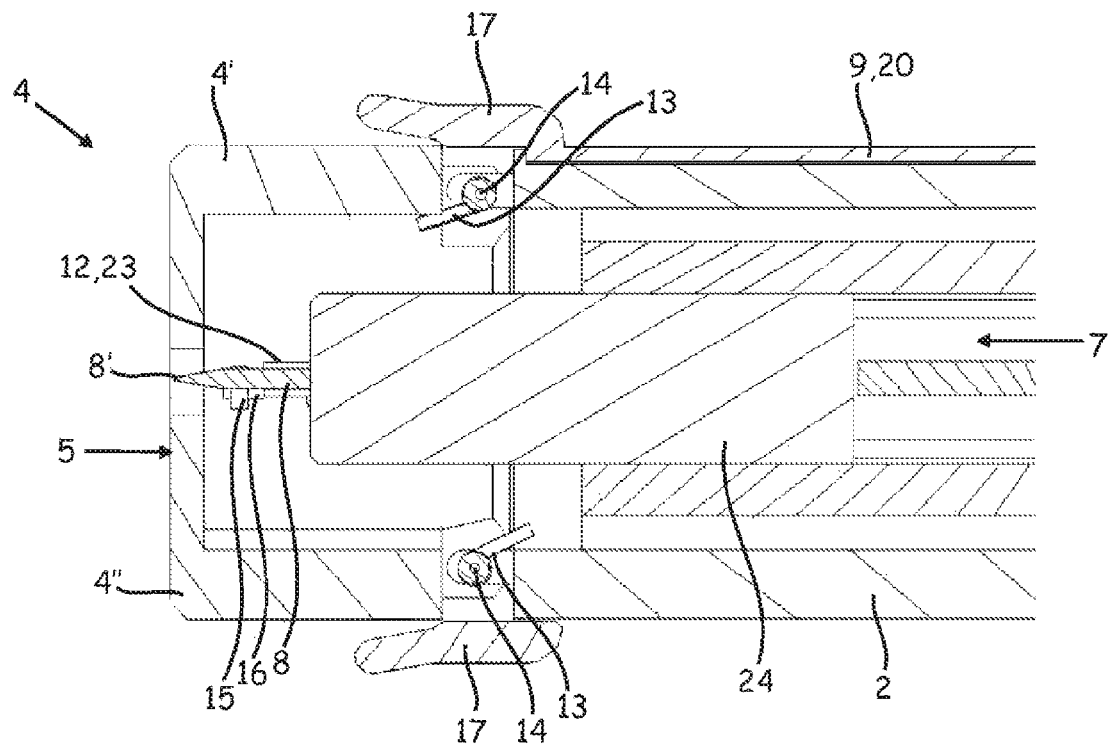
Figure 9:
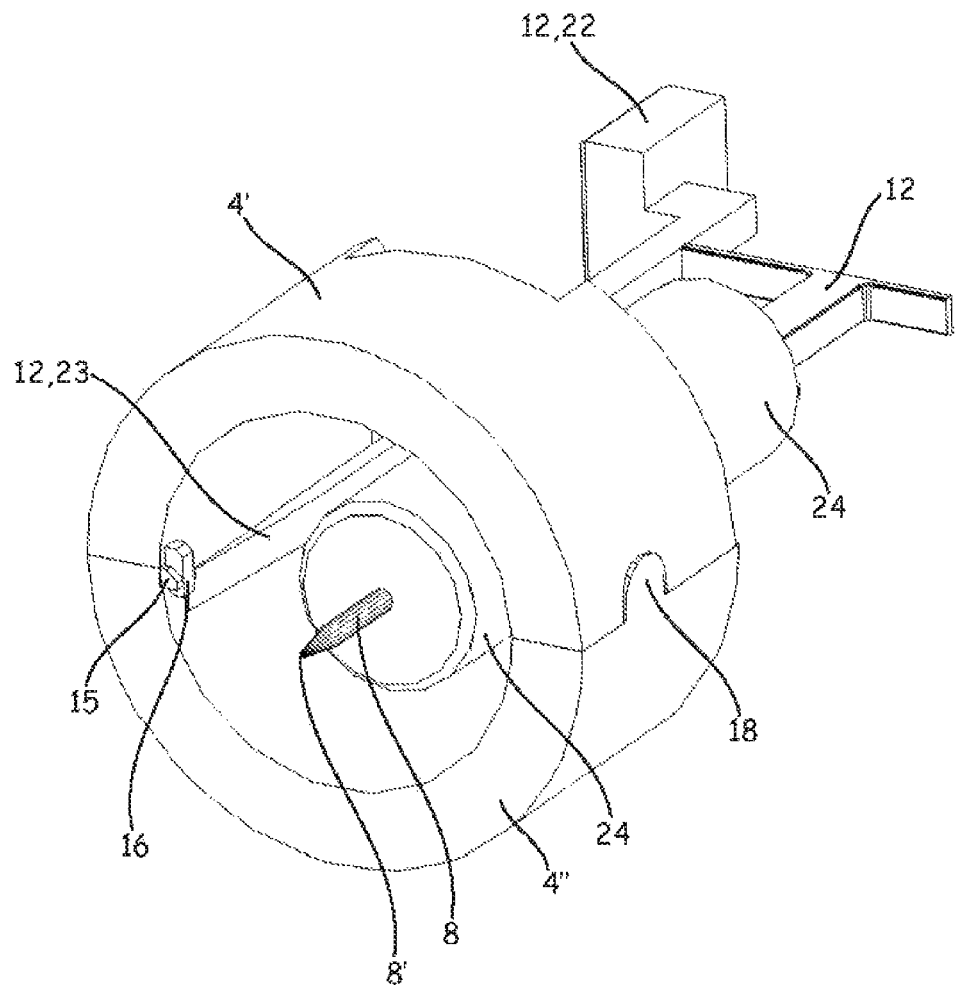

The figures show:

FIG. 1: perspective view of an embodiment of a lancing device according to the invention with closed endcap, FIG. 2: perspective view of the lancing device from FIG. 1 with endcap open, FIG. 3: detailed view of the front end of the lancing device from FIG. 2, FIG. 4: cross-section of the lancing device from FIG. 3, FIG. 5: a side view of an embodiment of a lancing device according to the invention, FIG. 6: perspective view of the lancing device from FIG. 5 with a locking element in a second position, FIG. 7: cross-section through an embodiment of a lancing device according to the invention with endcap closed, FIG. 8: lancing device from FIG. 7 with displaced clamping device and FIG. 9: an embodiment of an ejection device of a lancing device according to the invention, FIG. 1 shows a perspective view of an embodiment of a lancing device 1 according to the invention. This lancing device 1 substantially comprises a pen-like body 2 that can hold at least one lancet 8. At the end 3 of the body there is an endcap 4, which can serve to cover the lancet 8 arranged inside the lancing device 1 or the body 2. In the view in FIG. 4 the endcap 4 is in the closed position.

The endcap 4 is made up of two portions 4' und 4", which are pivotably arranged against each other on the body 2 by means of a pivot joint 14 around an axis perpendicular to the direction of displacement of the lancet 8 in the lancing device 1. The endcap 4 also has a positioning surface 5, with which the lancing device 1 can be positioned on the application site. Within the positioning surface 5 the endcap 4 has an outlet opening 6 for the tip 8' of the lancet 8.

Actuating elements 20, 21 and 22 of a clamping device 9, a release mechanism 10 and an ejection device 12 are arranged on the casing of the body 2 of the lancing device 1. The actuating element of the clamping device is designed as a clamping slider, that of the release mechanism 10 as a release button 21 and that of the ejection device 12 as an ejection slider 22. A sliding element 17 designed as a locking ring and running around the circumference of the body is arranged on the casing of the body 2 of the lancing device 1 and can be used to move the two portions 4' and 4" of the endcap 4 from the open position into the closed position.

In the view in FIG. 2 the endcap 4 of the lancing device 1 is in the open position, in which a lancet 8 can be ejected from the lancing device 1. One can clearly see how the lancet 8 is retained with its lancet body 24 in the socket 7 inside the body 2 of the lancing device 1.

Additional elements of the endcap 4 can be seen in the view in FIG. 4. These include interlocking latching elements 18 and 19 of the portions 4' und 4", which ensure that the two portions 4' und 4" of the endcap 4 are always correctly positioned relative to each other on closing so that the positioning surface 5 of the lancing device 1 is always even when the endcap 4 is closed. At least for portion 4" of the endcap 4 one can also see the pivot joint 14, which is coupled with a spring element 13, so that when the endcap 4 is closed the spring elements 13 exert a force on the individual portions 4' und 4" which strives to move the portions 4' und 4" of the endcap 4 out of the closed position shown in FIG. 1 into the open position shown in FIG. 2. So that this not only serves to eject a used Lancet 8, locking elements 15 and 16 are arranged in the portions 4' und 4" of the endcap 4, said locking elements being designed as snap-in hooks and snap-in elements and locking portions 4' und 4" of the endcap 4 together in the closed position.

In the closed position these locking elements 15, 16 are engaged. In order to disengage them, a contact element 23 is arranged on the ejection device 12 or the ejection slider 22 and this disengages the locking elements 15 and 16 when the ejection slider 23 is slid towards the end 3 of the lancing device 1, so that portions 4' und 4" of the endcap 4 automatically pivot out of the closed position shown in FIG. 1 into the open position shown in FIG. 2 under the spring force of the pivot joint 14 due to the spring elements 13.

The view in FIG. 3 shows the front end 3 of the lancing device 1 shown in FIG. 2 in greater detail. In this view one can see in particular the interlocking latching means 18 and 19 of portions 4' and 4" of the endcap and their locking elements 15 and 16 and the contact element 23 of the ejection device 12.

FIG. 4 shows another detailed view of the front end 3 of the lancing device 1 from FIG. 2, however this time in cross-section. In this view one can clearly see how the lancet 8 with its lancet body 24 is held in the socket 7 of the body 2 of the lancing device 1. One can also see the two pivot joints 14 of the respective portions 4' and 4" of the endcap 4 with their corresponding spring elements 13 and their locking elements 15 and 16.

One can also clearly see that the slider element 17 of the clamping device 9 engages in portions 4' and 4" of the endcap 4 when it is slid towards the end 3 of the lancing device where the endcap 4 is located and said slider element pivots said portions around the pivot joint 14 against the force of the spring elements 13 until the locking elements 15 and 16 of portions 4' and 4" engage in each other and mutually interlock so that the endcap once again adopts its closed position.

FIG. 5 shows the lancing device at the start of a clamping process or the insertion of a new lancet 8. The lancet has been manually inserted into the socket 7 of the body 2 of the lancing device 1 but the clamping slider 20 of the clamping device 9 has not yet been actuated.

FIG. 6 shows the lancing device 1 during actuation of the clamping slider 20 of the clamping device 9. The clamping slider 20 has travelled over its maximum course and the sliding element 17 is just about to pivot portions 4' and 4" of the endcap 4 towards each other until the locking elements 15 and 16 of portions 4' and 4" engage with each other and lock the endcap 4 in the closed position. In this view the two portions 4' and 4" of the endcap 4 are just short of their closed position, just before the point where locking elements 15 and 16 engage with each other.

FIG. 8 shows a cross-sectional view of this closed position. In this view the slider element 17 designed as a locking ring is in the extended position over the endcap 4 or its portions 4' and 4", in which position the locking elements 15 and 16 of the portions 4' and 4" are already engaged in each other, thereby holding the endcap 4 in this closed position. This view also shows very clearly that the tip 8' of the lancet 8 no longer projects through the opening 6 in the positioning surface 5 of the endcap 4 and is held safely inside the lancing device 1 to prevent any risk of injury from the tip 8' of the lancet 8.

In the view in FIG. 7 the clamping process has now been completed and the sliding element 17 designed as a locking ring has returned to its original position, in which it no longer extends over the endcap 4 or its portions 4' and 4". The tip 8' of the lancet 8 is still not projecting through the opening 6 in the positioning surface 5 of the endcap 4 and is therefore safely held inside the lancing device 1 to prevent any risk of injury from the tip 8' of the lancet 8. In this state the lancet 8 is clamped inside the lancing device 1. The lancing device 1 is ready to perform a lancing procedure. This can now be initiated by actuating the release element 21 of the release mechanism 10, once the positioning surface is placed on the application site.

Finally, FIG. 9 shows an embodiment of an ejection device 12, over which is arranged an endcap 4 consisting of two portions 4' and 4", the positioning surface 5 not being shown in this case. The said ejection device 12 is formed all in one piece together with contact element 23 and ejection slider 22. When the ejection slider 22 is pushed, the whole ejection device 12 moves with it. In the extreme position the contact element 23 engages in the locking elements 15 and 16 of portions 4' and 4" of the endcap 4 and disengages them so that the endcap 4 moves from its closed position into the open position and the used lancet is pushed out of the lancing device or its body 2 by the ejection device 12 and thereby ejected.

Below follows a brief description of a lancing procedure. Initially there is no lancet 8 in the lancing device. If the endcap 4 is still closed, it is opened by actuating the ejection slider 22 of the ejection device 10. This disengages locking elements 15 and 16 and the portions 4' and 4" of the endcap 4 are pivoted around the pivot joint 14 by the force of the spring elements 13 and moved from the closed position into the open position. In this position the lancet 8 is now manually inserted into the lancing device 1. Once the lancet 8 with the lancet body 24 is accurately positioned in the corresponding socket 7 of the lancing device 1 or its body 2, the sterile cover can be removed from the lancet. The lancet 8 is then clamped in the lancing device 1 by actuating the clamping slider 20 of the clamping device 9. As already described in detail above, the two portions 4' and 4" of the endcap 4 are hereby pivoted around the pivot joint 14 against the spring force of the spring elements 13 and the endcap 4 is closed. Once the clamping process is completed the endcap is kept in the closed position, since the locking elements 15 and 16 of the two portions 4' and 4" of the endcap are mutually interlocked. The lancing device 1 is now ready for lancing. To do this, it is positioned with the positioning surface 5 of the endcap 4 on the application site and the release element 21 of the release mechanism 10 is actuated. This pushes the tip 8' of the lancet 8 through the outlet opening 6 in the positioning surface 5 of the endcap 4 to a preset lancing depth, the release mechanism 10 building up a retraction force during the lancing process. This retraction force withdraws the lancet 8 back inside the lancing device so that the tip of the lancet 8 no longer protrudes through the outlet opening but is kept safely inside it to prevent any risk of injury from the tip 8' of the lancet 8. The used lancet 8 can now be ejected from the lancing device 1 by actuating the ejection slider 22 of the ejection device 12, as previously described, and be disposed of.

LIST OF REFERENCE NUMERALS

1 Lancing device
2 Body
3 End of lancing device
4 Endcap
4' Portion of the endcap
4" Portion of the endcap
5 Positioning surface
6 Outlet opening
7 Socket
8 Lancet
8' Lancet tip
9 Clamping device
10 Release mechanism
12 Ejection device
13 Spring element
14 Pivot joint
15 Locking element
16 Locking element
17 Sliding element
18 Latching means
19 Latching means
20 Clamping slider
21 Release element
22 Ejection slider
23 Contact element
24 Lancet body

The invention claimed is:

1. A lancing device for collecting body fluid samples, comprising:
   a) a body, at the end of which an endcap is arranged, said endcap having a positioning surface with an outlet opening,
   b) a socket to receive at least one lancet, wherein said lancet is interchangeably clamped in the body,
   c) a clamping device, with which the lancet is clamped inside the body, and a release mechanism able to initiate a lancing procedure, a tip of said lancet emerging through the outlet opening during the lancing procedure, and
   d) an ejection device to eject said lancet after the lancing procedure, wherein the endcap comprises several portions, each of said portions is pivotably connected via a separate pivot joint to said body, wherein the endcap is functionally coupled with the ejection device in such a way that, when the ejection device is actuated, said several portions pivot against each other, around an axis perpendicular to a direction of displacement of said lancet so that said several portions can move out of an ejection path of said lancet.

2. The lancing device according to claim 1, wherein each of said pivot joints are spring loaded by a spring element.

3. The lancing device according to claim 2, wherein the portions of the endcap comprise interlocking, detachable locking elements.

4. The lancing device of claim 3, wherein the interlocking, detachable locking elements are snap-in hooks and corresponding snap-in elements.

5. The lancing device according to claim 2, wherein the portions of the endcap comprise interlocking latching means.

6. The lancing device of claim 2, wherein the endcap comprises two portions.

7. The lancing device according to claim 1, wherein the endcap is functionally coupled with the clamping device in such a way that the endcap can be automatically swivelled out of an open position into a closed position for clamping the lancet in the body.

8. The lancing device according to claim 7, wherein the clamping device comprises a sliding element, which can be slid at least partially over the endcap while the lancet is clamped in the body, wherein the sliding element when slid over the endcap engages the portions of the endcap causing the endcap to swivel out of an open position into a closed position.

9. The lancing device according to claim 8, wherein the sliding element is designed as a locking ring.

10. The lancing device of claim 9, wherein the body is substantially cylindrical in shape.

11. The lancing device according to claim 1, wherein the clamping device comprises a clamping slider.

12. The lancing device of claim 11, wherein the clamping slider is arranged on the surface of the body.

13. The lancing device according to claim 1, wherein the release mechanism comprises a release element.

14. The lancing device of claim 13, wherein the release element is arranged on the surface of the body.

15. The lancing device of claim 13, wherein the release element is a release button.

16. The lancing device according to claim 1, wherein the ejection device comprises an ejection slider.

17. The lancing device of claim 16, wherein the ejection slider is arranged on the surface of the body.

18. The lancing device according to claim 1, wherein the ejection device comprises a contact element, with which locking elements are disengaged for ejecting said lancet after the lancing procedure.

19. The lancing device of claim 18, wherein the locking elements are snap-in hooks and corresponding snap-in elements.

20. A lancing device for collecting body fluid samples, comprising:
   a) a body, at the end of which an endcap is arranged, said endcap having a positioning surface with an outlet opening;
   b) a socket to receive at least one lancet, wherein said lancet is interchangeably clamped in the body;

c) a clamping device, with which the lancet is clamped inside the body and a release mechanism able to initiate a lancing procedure, a tip of said lancet emerging through the outlet opening during the lancing procedure;
d) an ejection device, to eject said lancet after the lancing procedure; and
e) a sliding element, which can be slid at least partially over the endcap while the lancet is clamped in the body, wherein the endcap is functionally coupled with the ejection device in such a way that, when the ejection device is actuated, said endcap is held pivotably on the body so that it can move out of an ejection path of said lancet, wherein the endcap comprises several portions, and wherein the sliding element when slid over the endcap engages the portions of the endcap causing the endcap to swivel out of an open position into a closed position.

* * * * *